United States Patent
Morrison et al.

(10) Patent No.: US 7,754,924 B2
(45) Date of Patent: Jul. 13, 2010

(54) PROCESS FOR THE MONOSULFONATION OF AROMATIC PHOSPHINES, AND ZWITTERIONIC PRODUCT DERIVED THEREFROM

(75) Inventors: Donald L. Morrison, Fort Collins, CO (US); Kurt D. Olson, Freeland, MI (US); Walter C. Reed, Advent, WV (US); Anthony G. Abatjoglou, Charleston, WV (US)

(73) Assignee: Dow Global Technologies Inc., Midland, MI (US)

( * ) Notice: Subject to any disclaimer, the term of this patent is extended or adjusted under 35 U.S.C. 154(b) by 200 days.

(21) Appl. No.: 12/064,064

(22) PCT Filed: Sep. 14, 2006

(86) PCT No.: PCT/US2006/036123
§ 371 (c)(1),
(2), (4) Date: Feb. 18, 2008

(87) PCT Pub. No.: WO2007/035540
PCT Pub. Date: Mar. 29, 2007

(65) Prior Publication Data
US 2008/0221363 A1    Sep. 11, 2008

Related U.S. Application Data
(60) Provisional application No. 60/717,549, filed on Sep. 15, 2005.

(51) Int. Cl.
C07F 5/02 (2006.01)
(52) U.S. Cl. ....................................... 568/13
(58) Field of Classification Search .............. 568/13
See application file for complete search history.

(56) References Cited

U.S. PATENT DOCUMENTS

| | | | |
|---|---|---|---|
| 5,180,854 | A | 1/1993 | Abatjoglou et al. |
| 5,451,698 | A | 9/1995 | Bahrmann et al. |
| 5,663,426 | A | 9/1997 | Albanese et al. |
| 5,684,181 | A | 11/1997 | Albanese et al. |
| 6,469,169 | B1 | 10/2002 | Seayad et al. |
| 6,610,881 | B1 | 8/2003 | Riedel et al. |
| 6,613,939 | B2 | 9/2003 | Aouni et al. |
| 6,790,985 | B2 | 9/2004 | Yada et al. |
| 6,864,387 | B2 | 3/2005 | Riedel et al. |
| 2006/0193802 | A1 | 8/2006 | Lysenko et al. |

FOREIGN PATENT DOCUMENTS

| | | |
|---|---|---|
| DE | 10123436 A1 | 5/2001 |
| EP | 0435073 | 7/1991 |
| WO | WO2004/096744 | 11/2004 |
| WO | WO2007/035540 A3 | 3/2007 |
| WO | WO2007/133379 | 11/2007 |

OTHER PUBLICATIONS

Hida et al. J.Coord. Chem. 1998, 43, 345-348.*
Amani et al. Organometallics 1989, 8, 542-547.*
Bartik, et al., *Inorganic Chemistry*, vol. 31, 1992, pp. 2667-2670.
H. Gulyás, et al., *European Journal of Organic Chemistry*, 2003, pp. 2775-2781.
B. Fell, et al., *Journal für praklische Chemie, Chemiker-Zeitung*, vol. 336, 1994, pp. 591-595.
S. Hida, et al., *Journal of Coordination Chemistry*, vol. 41, 1998, pp. 345-348.
A. J. Gordon and R. A. Ford, *The Chemist's Companion: A Handbook of Practical Data, Techniques, and References*, Wiley-Interscience Publishers, John Wiley & Sons, 1972, pp. 71-74.
T. Mussini, et al., "Criteria for Standardization of pH Measurements in Organic Solvents and Water," *Pure and Applied Chemistry*, 57 (1985), 865-876.
B. M. Bhanage, et al., "Selectivity in Sulfonation of Triphenyl Phosphine," *Organic Process Research & Development*, 4(5) Coden: Oprdfk; Issn: 1083-6160, 2000, pp. 342-345.
C. Ahrland et al., "The Relative Affinities of Co-ordinating Atoms for silver Ion Part II. Nitrogen, Phosphorous and Arsenic," *J. Chem. Soc.*, 1958, pp. 276-288.
Derwent 2002-164977 (CN 1179428, 20020409).

* cited by examiner

*Primary Examiner*—D. Margaret Seaman
*Assistant Examiner*—Nizal S Chandrakumar

(57) ABSTRACT

A method of preparing an aromatic phosphine monosulfonate in zwitterionic form, such as dicyclohexylphenylphosphine monosulfonate zwitterion, involving contacting an aromatic phosphine with a sulfonating agent to provide a reaction mixture containing aromatic phosphine monosulfonate in acid form and unconverted sulfonating agent; quenching or removing substantially all of the unconverted sulfonating agent; partially neutralizing the aromatic phosphine monosulfonate in acid form to phase separate aromatic phosphine monosulfonate in zwitterionic form as a solid or neat liquid layer; and collecting the zwitterion as a solid or neat liquid. The zwitterion may be neutralized to form the corresponding aromatic phosphine monosulfonate metal salt, which is useful in preparing catalysts for hydroformylation processes.

24 Claims, 3 Drawing Sheets

Graph of pH as a Function of Quantity of Base Added
for Titration of Dicyclohexylphenylphosphine Monosulfonate (A)

(B)

(C)

$^{31}$P NMR of Dicyclohexylphenylphosphine Monosulfonate Sodium Salt

PROCESS FOR THE MONOSULFONATION OF AROMATIC PHOSPHINES, AND ZWITTERIONIC PRODUCT DERIVED THEREFROM

This application is a 371 of International Patent Application No.
PCT/US2006/036123, filed Sep. 14, 2006, which claims the benefit of U.S. Provisional Application Ser. No. 60/717,549, filed Sep. 15, 2005.

BACKGROUND OF THE INVENTION

This invention pertains to a process for the sulfonation of aromatic phosphines, more particularly, the monosulfonation of aromatic phosphines to their corresponding monosulfonated derivatives.

Sulfonated aromatic phosphines find utility as ligands in transition metal-ligand complex catalysts that are useful, for example, in carbonylation processes, such as, hydroformylation processes that convert olefins to aldehydes. More particularly, aromatic phosphine monosulfonated metal salts are useful ligands in rhodium-organophosphine ligand complex catalysts, which are useful in hydroformylation processes to convert unsaturated fatty acids and fatty acid esters to their corresponding fatty acid and fatty acid ester aldehydes. These fatty acid aldehydes and fatty acid ester aldehydes can be further derivatized to the corresponding difunctionalized fatty acid and fatty acid ester alcohols, acids, or amines, which are useful intermediates in the preparation of thermoset polymers and epoxy resins.

Dialkyl monoaryl phosphine monosulfonate metal salts are particularly advantageous in that they tend to exhibit a high degree of activity in hydroformylation processes. Moreover, catalysts prepared with dialkyl monoaryl phosphine monosulfonate metal salts tend to exhibit less sulfonate and aryl group scrambling, thereby resulting in better catalyst selectivity and a higher degree of catalyst stability, as compared with catalysts containing sulfonated triarylphosphine ligand.

The syntheses of aromatic phosphine monosulfonates, disulfonates, or trisulfonates have been described in the art, as indicated for example by the following references: U.S. Pat. Nos. 5,451,698, 5,663,426, 5,684,181, 6,610,881 B1, 6,613,939 B2, and 6,864,387 B1; Bartik, et al., *Inorganic Chemistry*, vol. 31, 1992, pp. 2667-2670; H. Gulyás, et al., *European Journal of Organic Chemistry*, 2003, pp. 2775-2781; B. Fell, et al., *Journal für praktische Chemie, Chemiker-Zeitung*, vol. 336, 1994, pp. 591-595; and S. Hida, et al., *Journal of Coordination Chemistry*, vol. 41, 1998, pp. 345-348. The foregoing publications mention various problems attendant to sulfonation and work-up of the reaction mixture, including the formation of mixtures of mono-, di-, and trisulfonated products that are difficult to separate; the obtention of low yields of the desired sulfonated product; and the formation and presence in the product of impurity phosphine oxides, sulfites, and most particularly, metal sulfates. The cited publications describe complex work-up procedures of the reaction mixture involving a multitude of extraction steps to reach a purified form of the desired aromatic phosphine sulfonated product. Disadvantageously, the complexity of such work-up procedures makes commercialization of these syntheses cost prohibitive. Consequently, it would be desirable to discover an improved synthesis of a sulfonated aromatic phosphine, preferably, an aromatic phosphine monosulfonate metal salt, that avoids the recovery, impurity, and separation problems of prior art syntheses and that produces in only a few cost-effective steps a purified form of the desired monosulfonated product. It would also be desirable to recover the aromatic phosphine monosulfonate metal salt in high yield.

SUMMARY OF THE INVENTION

In one aspect, this invention provides for a process of preparing an aromatic phosphine monosulfonate in zwitterionic form, the process comprising:

(a) contacting an aromatic phosphine with a sulfonating agent under reaction conditions sufficient to obtain a product mixture comprising an acid form of an aromatic phosphine monosulfonate and unconverted sulfonating agent;

(b) quenching or removing substantially all of the unconverted sulfonating agent; and (c) partially neutralizing the acid form of the aromatic phosphine monosulfonate with an aqueous solution of a neutralizing agent under conditions sufficient to phase separate substantially all of the aromatic phosphine monosulfonate in zwitterionic form; and (d) collecting the aromatic phosphine monosulfonate in zwitterionic form as a solid or neat liquid.

For the purposes of this invention, the phrase "aromatic phosphine monosulfonate in zwitterionic form" shall be taken to mean a form in which a phosphorus atom of the phosphine is protonated and consequently quadrivalent and positively charged, while the sulfonate group is deprotonated and therefore negatively charged.

The process of this invention significantly improves the synthesis of monosulfonated aromatic phosphines as compared with prior art syntheses. The improvement derives from the unexpected discovery that partial neutralization of the synthesis mixture produces a zwitterionic form of the aromatic phosphine monosulfonate, which phase separates from the product mixture as an essentially pure compound, either as a precipitate or as a neat liquid. In contrast, selected prior art describes full neutralization of the synthesis mixture leading to precipitation of not only the desired sulfonated product but all sulfonated by-products as well as substantial quantities of metal sulfates, phosphine oxide, and possibly sulfites. Other prior art envisage multiple extractions to reach a purified form of the desired sulfonated product. In contrast, the present invention avoids multiple extractions by employing a partial neutralization to yield a substantially pure zwitterionic form of the desired monosulfonate, which zwitterion is readily converted to substantially pure aromatic phosphine monosulfonate in acid or salt form, as desired. Preferably, the zwitterion is converted to the aromatic phosphine monosulfonated metal salt, which provides for catalytically active transition metal-ligand complex catalysts for industrial processes, notably, carbonylation processes, most notably, hydroformylation processes. The claimed invention, in its simplicity, provides a more cost-effective method of preparing these valuable aromatic phosphine monosulfonate metal salts.

In another aspect, this invention provides for a solid or neat liquid aromatic phosphine monosulfonate in zwitterionic form, represented by the following formula (1):

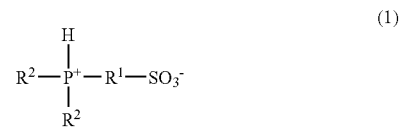

(1)

wherein $R^1$ represents a sulfonated monovalent hydrocarbyl radical containing from 1 to about 30 carbon atoms selected from aryl, alkaryl, and aralkyl monovalent radicals, such that the aryl group is sulfonated (as shown in the formula); and each $R^2$ individually represents a monovalent hydrocarbyl radical containing from 1 to about 30 carbon atoms.

The solid or neat liquid aromatic phosphine monosulfonate isolated in zwitterionic form may be readily converted to its corresponding aromatic phosphine monosulfonate salt, preferably, metal salt, in substantially purified form. As mentioned hereinbefore, a dialkylarylphosphine monosulfonate metal salt is beneficially employed in hydroformylation processes, most beneficially, in the hydroformylation of unsaturated fatty acid or fatty acid esters to their corresponding fatty acid or fatty acid ester aldehydes.

DRAWINGS

DETAILED DESCRIPTION OF THE INVENTION

Figure 1:
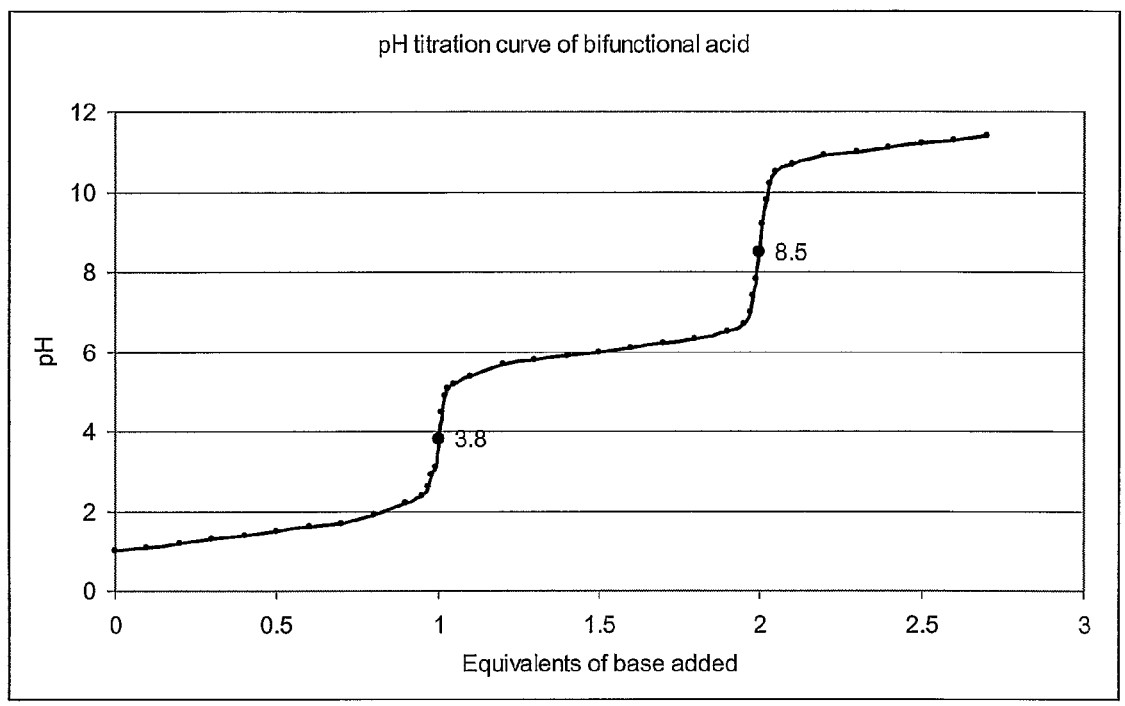
FIG. 1 is a graph illustrating a titration of dicyclohexylphenylphosphine monosulfonate. The graph plots pH as a function of equivalents of base added.

In the description herein and in the claims that follow, reference is made to certain chemical terms that shall be defined to have the following meanings.

As used herein, the term "aromatic phosphine" refers to a compound comprising a central phosphorus atom bonded via three phosphorus-carbon bonds to three hydrocarbyl groups, which latter term includes substituted hydrocarbyl groups, heteroatom-containing hydrocarbyl groups, and substituted heteroatom-containing hydrocarbyl groups, provided that at least one of said hydrocarbyl groups is an aryl, alkaryl, or aralkyl group or a substituted variant thereof. In accordance with this definition for this invention, the term "aromatic phosphine" is broadly intended to include (a) compounds wherein an aryl group is bonded directly to the phosphorus atom, and (b) compounds wherein an aryl group is bonded to an alkyl group which itself is bonded to the phosphorus atom. A non-limiting example of (a) is "dicyclohexylphenylphosphine." A non-limiting example of (b) is "dicyclohexyl-α-phenylethylphosphine."

The term "aromatic phosphine monosulfonate" refers to an aromatic phosphine as noted hereinabove wherein one sulfonate moiety replaces one hydrogen atom in an aryl ring of said aryl, alkaryl, or aralkyl group.

As used herein, the phrase "aromatic phosphine monosulfonate in acid form" refers to an embodiment of the sulfonated aromatic phosphine in which the sulfonate group and a phosphorus atom are both protonated.

As used herein, the phrase "zwitterionic form of the aromatic phosphine monosulfonate" is taken to mean an embodiment of the sulfonated aromatic phosphine in which a phosphorus atom is protonated (and consequently quadrivalent and positively charged (+1)), whereas the sulfonate group is deprotonated and thus negatively charged (−1).

As used herein, the phrase "aromatic phosphine monosulfonate salt" is taken to mean an embodiment of the sulfonated aromatic phosphine in which the sulfonate group is deprotonated and therefore negatively charged (−1) and is associated for charge balance with a cation, such as a monovalent metal ion (e.g., $Na^{+1}$), or a quaternary ammonium ion or quaternary phosphonium ion.

The term "hydrocarbyl" refers to univalent organic radicals comprised of carbon and hydrogen atoms and containing from about 1 to about 30 carbon atoms, preferably, from 1 to about 12 carbon atoms, including linear, branched, cyclic, saturated and unsaturated species, such as alkyl, alicyclic, alkenyl, aryl, alkaryl, and aralkyl groups. "Substituted hydrocarbyl" shall refer to a hydrocarbyl group that is substituted with one or more substituents, as defined hereinafter. "Heteroatom-containing hydrocarbyl" shall refer to a hydrocarbyl group wherein at least one heteroatom, preferably, nitrogen (N), phosphorus (P), oxygen (O), sulfur (S), or silicon (Si), is present.

The term "hydrocarbylene" refers to a divalent hydrocarbyl group.

The term "aryl" refers to a monovalent aromatic radical containing a single aromatic ring or containing multiple aromatic rings that are fused together or directly linked, or indirectly linked (such that different aromatic groups are bound through a common group, such as methylene or ethylene). Preferred aryl groups contain one aromatic ring, or 2 to 4 fused or linked aromatic rings, for example, phenyl, naphthyl, biphenyl, and the like.

The term "arylene" refers to a divalent aryl group, where aryl is as defined hereinabove.

The term "alkaryl" refers to an monovalent aryl group with one or more alkyl substituents. The term "alkarylene" refers to a divalent aryl group with one or more alkyl substituents.

The term "alkyl" refers to a linear, branched, or cyclic (alicyclic) saturated hydrocarbyl monovalent radical, typically, though not necessarily containing from 1 to about 20 carbon atoms, for example, methyl, ethyl, propyl, isopropyl, and the like, as well as cyclic groups (alicyclic) that typically contain from about 4 to about 8 carbon atoms, such as cyclopentyl, cyclohexyl, and cyclooctyl. Preferably, the alkyl group will contain from about 1 to about 12 carbon atoms; and the cycloalkyl group will contain from about 5 to about 7 carbon atoms.

The term "alkylene" as used herein refers to a divalent linear, branched, or cyclic alkyl group, wherein "alkyl" is as defined hereinabove.

The term "aralkyl" refers to a monovalent alkyl group substituted with an aryl group. The term "aralkylene" refers to a divalent alkylene group substituted with an aryl group.

As used herein, any and all of the terms "hydrocarbyl," "hydrocarbylene," "alkyl," "alkylene," "aryl," "arylene," "alkaryl," "alkarylene," "aralkyl," "aralkylene," and "alicyclic" are intended to include substituted variants thereof or variants that contain a heteroatom. The term "substituted" or the words "substituted variants thereof" generally refer to the replacement of at least one hydrogen atom that is bonded to a carbon atom, for example, an alkyl or aryl carbon atom, with a non-hydrogen moiety, including without limitation functional groups such as halogen, sulfinato, $C_{1-20}$ alkylsulfanyl, $C_{5-20}$ arylsulfonyl, $C_{1-20}$ alkylsulfonyl, $C_{5-20}$ arylsulfonyl, $C_{1-20}$ alkylsulfinyl, $C_{5-20}$ arylsulfinyl, sulfonamide, phosphonyl, amino, amido, imino, nitro, hydroxyl, $C_{1-20}$ alkoxy, $C_{5-20}$ aryloxy, $C_{2-20}$ alkoxycarbonyl, $C_{5-20}$ aryloxycarbonyl, carboxylate, mercapto, formyl, acyl, $C_{1-20}$ thioester, cyano, cyanato, carbamoyl, epoxy, styrenyl, silyl, silyloxy, silanyl, siloxazanyl, and the hydrocarbyl moieties $C_{1-20}$ alkyl, $C_{2-20}$ alkenyl, $C_{2-20}$ alkynyl, $C_{5-20}$ aryl, $C_{5-30}$ aralkyl, and $C_{5-30}$ alkaryl. In addition, the aforementioned functional groups may, if a particular group permits, be further substituted with one or more additional functional groups or with one or more hydrocarbyl moieties, such as those specifically enumerated above.

References made herein to groups in the Periodic Table of the Elements are made with respect to the Periodic Table of the IUPAC (1985).

As described hereinbefore, the process of this invention pertains to a simple, cost-effective synthesis of an aromatic phosphine monosulfonate zwitterion in substantially purified form, which zwitterion may be readily converted, preferably, to aromatic phosphine monosulfonate metal salt of substantially purified form. Consequently, in a first aspect, this invention provides for a process of preparing an aromatic phosphine monosulfonate in zwitterionic form, the process comprising:

(a) contacting an aromatic phosphine with a sulfonating agent under reaction conditions sufficient to obtain a product mixture comprising an acid form of an aromatic phosphine monosulfonate and unconverted sulfonating agent;

(b) quenching or removing substantially all of the unconverted sulfonating agent; and (c) partially neutralizing the acid form of the aromatic phosphine monosulfonate with an aqueous solution of a neutralizing agent (first neutralizing agent) under conditions sufficient to phase separate substantially all of the aromatic phosphine monosulfonate in zwitterionic form; and (d) collecting the aromatic phosphine monosulfonate in zwitterionic form as a solid or neat liquid.

As a further step subsequent to (d), optionally, (e) the solid or neat liquid aromatic phosphine monosulfonate in zwitterionic form is contacted with a liquid medium to form a solution or slurry and thereafter neutralized with a second neutralizing agent under conditions sufficient to yield an aromatic phosphine monosulfonate salt.

As used herein, the phrase "quenching or removing substantially all of the unconverted sulfonating agent" shall mean quenching or removing typically greater than about 50, preferably, greater than about 70, more preferably, greater than about 80, even more preferably, greater than about 90, and most preferably, greater than about 98 weight percent of the unconverted sulfonating agent.

The skilled artisan will recognize that the words "phase separate" refer to the act of parting or disjoining two or more components of a one-phase mixture such as to form two or more immiscible phases (namely, solid+liquid phases, or two distinct liquid layers). More specifically, the zwitterion precipitates as a solid phase or separates into a neat liquid phase that is distinct from the liquid phase in which the neutralization occurs.

As used herein, the phrase "sufficient to phase separate substantially all of the aromatic phosphine monosulfonate in zwitterionic form" shall mean to phase separate typically greater than about 70, preferably, greater than about 80, more preferably, greater than about 90, even more preferably, greater than about 95, and most preferably, greater than about 98 weight percent of the total aromatic phosphine monosulfonate as the zwitterionic species.

In a preferred embodiment, the process of this invention provides for a method of preparing a dialkylarylphosphine monosulfonate in zwitterionic form, the process comprising:

(a) contacting a dialkylarylphosphine with oleum under reaction conditions sufficient to obtain a product mixture comprising an acid form of a dialkylarylphosphine monosulfonate and unconverted oleum;

(b) quenching or removing substantially all of the unconverted oleum; and (c) partially neutralizing the acid form of the dialkylarylphosphine monosulfonate with an aqueous solution of a neutralizing agent (first neutralizing agent) under conditions sufficient to phase separate substantially all of the dialkylarylphosphine monosulfonate in zwitterionic form; and (d) collecting the dialkylarylphosphine monosulfonate in zwitterionic form as a solid or neat liquid.

Subsequent to step (d), optionally, in a further step, (e) the zwitterion collected as a solid or neat liquid may be contacted with a liquid medium to form a solution or a slurry and thereafter neutralized with a second neutralizing agent under conditions sufficient to yield a dialkylarylphosphine monosulfonate salt.

In a more preferred embodiment, the aryl group on the dialkylarylphosphine comprises phenyl or a substituted phenyl group.

In a most preferred embodiment, the process of this invention provides for a method of preparing a dicyclohexylphenylphosphine monosulfonate in zwitterionic form, the process comprising:

(a) contacting dicyclohexylphenylphosphine with oleum under reaction conditions sufficient to obtain a product mixture comprising an acid form of the dicyclohexylphenylphosphine monosulfonate and unconverted oleum;

(b) quenching or removing greater than about 90 weight percent of the unconverted oleum; and (c) partially neutralizing the acid form of the dicyclohexylphenylphosphine monosulfonate with an aqueous solution of a neutralizing agent (first neutralizing agent) to a pH of about 3.8±1.0, so as to precipitate substantially all of the dicyclohexylphenylphosphine monosulfonate in solid zwitterionic form; and (d) collecting the solid precipitate comprising dicyclohexylphenylphosphine monosulfonate in zwitterionic form.

Subsequent to (d), optionally, as a further step, (e) the precipitate comprising dicyclohexylphenylphosphine monosulfonate zwitterion is contacted with a $C_{1-4}$ alcohol and thereafter neutralized with a $C_{1-4}$ alcohol solution of an alkali metal hydroxide to a pH of about 8.5±1.0 sufficient to obtain dicyclohexylphenylphosphine monosulfonate alkali metal salt.

In a most preferred embodiment, the dicyclohexylphenylphosphine monosulfonate alkali metal salt comprises dicyclohexylphenylphosphine monosulfonate sodium salt.

In another preferred embodiment, the neutralizing agent to form the zwitterion (first neutralizing agent) and the second neutralizing agent to form the metal salt both comprise sodium hydroxide.

In a second aspect, this invention provides for an aromatic phosphine monosulfonate in zwitterionic form isolated as a solid or neat liquid and represented by the following formula (1):

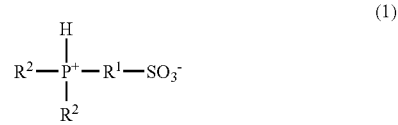

(1)

wherein $R^1$ represents a sulfonated monovalent hydrocarbyl radical containing from 1 to about 30 carbon atoms selected from aryl, alkaryl, and aralkyl monovalent radicals, such that the aryl group is sulfonated as shown; and each $R^1$ individually represents a monovalent hydrocarbyl radical containing from 1 to about 30 carbon atoms.

In a preferred second aspect, this invention provides for a dialkylarylphosphine monosulfonate in zwitterionic form, isolated as a solid or neat liquid, and represented by formula (1) hereinabove, wherein $R^1$ represents a sulfonated monovalent hydrocarbyl radical containing from 1 to about 30 carbon atoms selected from aryl, alkaryl, and aralkyl monovalent radicals, such that the aryl group is sulfonated as shown, and each $R^2$ individually represents a monovalent hydrocarbyl radical containing from 1 to about 30 carbon atoms selected from the class of alkyl and alicyclic monovalent radicals, including wherein $R^1$ and $R^2$ may be unsubstituted or substituted variants thereof.

In a more preferred embodiment, $R^1$ is phenyl, and each $R^2$ is dicyclohexyl; and the compound comprises dicyclohexylphenylphosphine monosulfonate in zwitterionic form, isolated as a solid or neat liquid, and represented by formula (2):

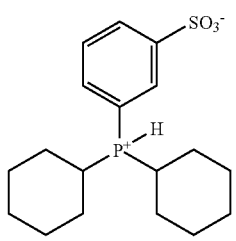

(2)

In another aspect, the detailed description that follows may be readily extended to disulfonating an aromatic phosphine to yield a fully protonated form of a disulfonated aromatic phosphine, which it is believed may be partially neutralized to phase separate an insoluble precipitate or a neat liquid phase of a disulfonated aromatic phosphine in zwitterionic form.

The aromatic phosphine to be monosulfonated in the process of this invention comprises any monophosphine, biphosphine, triphosphine, oligophosphine, or polyphosphine that contains at least one aromatic radical bonded to at least one trivalent phosphorus atom. In addition to phenyl radicals, aromatic radicals also include ring assemblies directly linking two or more aryl radicals through a C—C bond, for example, biphenyl; and ring assemblies indirectly linking two or more aryl radicals through a common group, such as a methylene or ethylene, for example, 4-benzylphenyl; and fused ring systems, such as naphthyl or indenyl radicals. One preferred form of the aromatic phosphine comprises a monophosphine represented by formula (3):

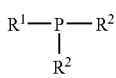

(3)

wherein $R^1$ represents a monovalent hydrocarbyl radical containing from 1 to about 30 carbon atoms selected from aryl, alkaryl, and aralkyl monovalent radicals; and each $R^2$ individually represents a monovalent hydrocarbyl radical containing from 1 to about 30 carbon atoms, preferably, selected from the class of alkyl, aryl, alkaryl, aralkyl, and alicyclic monovalent radicals, more preferably, alkyl and alicyclic monovalent radicals. Even more preferably, $R^1$ represents a monovalent hydrocarbyl radical containing from 1 to about 30 carbon atoms selected from aryl and alkaryl monovalent radicals; and each $R^2$ individually represents a monovalent hydrocarbyl radical containing from 1 to about 30 carbon atoms selected from alkyl and alicyclic monovalent radicals.

Another preferred form of the aromatic phosphine comprises a biphosphine represented by formula (4):

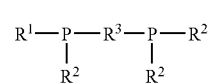

(4)

wherein $R^1$ and $R^2$ have the same meaning as defined in connection with formula (3) hereinabove; and $R^3$ is a divalent hydrocarbylene diradical of from 1 to about 30 carbon atoms, preferably, selected from the class of alkylene, arylene, alkarylene, aralkylene, and alicyclic divalent radicals.

Another preferred form of the aromatic phosphine is a triphosphine represented by formula (5):

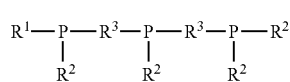

(5)

wherein $R^1$, $R^2$, and $R^3$ are identical to the those groups identified hereinabove in connection with formulas (3) and (4). More preferably, with respect to the biphosphine and triphosphine of formulas (4) and (5), $R^1$ represents a monovalent hydrocarbyl radical containing from 1 to about 30 carbon atoms selected from aryl and alkaryl monovalent radicals; each $R^2$ individually represents a monovalent hydrocarbyl radical containing from 1 to about 30 carbon atoms selected from allyl and alicyclic monovalent radicals; and each $R^3$ individually represents an alkylene or alicyclic diradical of from 1 to about 15 carbon atoms.

Non-limiting examples of suitable monovalent alkyl radicals include linear or branched, primary, secondary, or tertiary alkyl radicals, such as methyl, ethyl, n-propyl, iso-propyl, butyl, sec-butyl, t-butyl, t-butylethyl, t-butylpropyl, n-hexyl, amyl, sec-amyl, t-amyl, 2-ethylhexyl, n-octyl, iso-octyl, decyl, dodecyl, octadecyl, and eicosyl. Non-limiting examples of suitable monovalent aryl radicals include phenyl, biphenyl, and naphthyl. Non-limiting examples of suitable monovalent aralkyl radicals include benzyl and phenylethyl. Non-limiting examples of suitable monovalent alkaryl radicals include tolyl and xylyl. Non-limiting examples of suitable monovalent alicyclic radicals include cyclopentyl, cyclohexyl, cyclooctyl, and cyclohexylethyl.

Non-limiting examples of suitable alkylene diradicals include ethylene (—$CH_2CH_2$—), trimethylene (—$CH_2CH_2CH_2$—), tetramethylene (—$CH_2CH_2CH_2CH_2$—), higher homologues and branched homologues thereof. Non-limiting examples of suitable arylene diradicals include phenylene, naphthdiyl, biphenyldiyl, and the like. Non-limiting examples of suitable aralkylene diradicals include phendimethyl and phendiethyl. Non-limiting examples of suitable alkarylene diradicals include methylphenylene, dimethylphenylene. Non-limiting examples of suitable divalent alicyclic radicals include cyclopentylene and cyclohexylene.

In addition, the aforementioned monovalent and divalent hydrocarbyl radicals may bear one or more substituents that do not unduly interfere with the desired outcome of this process invention. Illustrative substituents that may be present on the monovalent hydrocarbyl radicals include, for example, alkyl radicals having from 1 to about 15 carbon atoms; silyl radicals such as —Si($R^4$)$_3$, acyl radicals such as —C(O)$R^4$, amido radicals such as —CON($R^4$)$_2$ and —N$R^4$CO($R^4$), sulfonyl radicals such as —SO$_2R^4$, alkyloxy radicals such as —O$R^4$, thionyl radicals such as —S$R^4$, phosphonyl radicals such as —P(O)($R^4$)$_2$, as well as halogen (Cl, F), nitro, cyano, trifluoromethyl, and hydroxy radicals, wherein each R may be the same or different and individually represents a substituted or unsubstituted monovalent hydrocarbyl radical having from 1 to about 20 carbon atoms. Other suitable substituents are mentioned hereinabove.

Non-limiting examples of suitable aromatic monophosphines that can be sulfonated by the process of this invention include dimethylphenylphosphine, diethylphenylphosphine, diisopropylphenylphosphine, dicyclopentylphenylphosphine, dicyclohexylphenylphosphine, and the like. Non-limiting examples of suitable aromatic biphosphines that can be sulfonated by the process of this invention include 2,2'-bis-(methylphenylphosphino)-1,1'-biphenyl, 4,4'-bis(methylphenylphosphino)-1,1'-biphenyl, 2,2'-bis(cyclohexylphenylphosphino)-1,1'-biphenyl, 4,4'-bis(cyclohexylphenylphosphino)-1,1'-biphenyl, and 2,2'-bis(methylphenylphosphino)binaphthyl, and 2,2'-bis(cyclohexylphenylphosphino)binaphthyl.

More preferably, $R^1$ is phenyl or a substituted phenyl. More preferably, each $R^2$ is individually a substituted or unsubstituted monovalent alicyclic radical of from about 5 to about 12 carbon atoms. Even more preferably, each $R^2$ is cyclohexyl or a substituted cyclohexyl. Preferably, $R^3$ is an alkylene diradical of from 1 to about 10 carbon atoms; or an arylene diradical of from about 6 to about 12 carbon atoms. Most preferably, $R^3$ is ethylene (—CH$_2$CH$_2$—). In a preferred form, the aromatic phosphine is a dicycloalkylphenylphosphine. Most preferably, the aromatic phosphine is dicyclohexylphenylphosphine or a substituted derivative thereof. Suitable substituents for any of the aforementioned species are described hereinbefore.

In the first step of this process invention, the aromatic phosphine is contacted in a reaction vessel with a sulfonating agent under reaction conditions sufficient to prepare the corresponding aromatic phosphine monosulfonate in acid form. Any sulfonating agent that produces the desired product may be suitably employed. Suitable sulfonating agents include, for example, oleum (fuming sulfuric acid, i.e., a solution of sulfur trioxide (SO$_3$) in sulfuric acid) or anhydrous mixtures of sulfuric acid and orthoboric acid, or gaseous sulfur trioxide (SO$_3$). Oleum is preferred, any commercial or non-commercial sample of which is acceptable for use. Preferred oleum has a concentration of sulfur trioxide (SO$_3$) equal to or greater than about 20 weight percent, preferably, equal to or greater than about 30 weight percent. A more preferred oleum has a concentration of from 20 to about 30 weight percent sulfur trioxide. Any molar ratio of sulfonating agent to aromatic phosphine may be employed that results in sulfonation of the phosphine to the desired aromatic phosphine monosulfonate. Preferably, the molar ratio of sulfonating agent to aromatic phosphine is not sufficiently high to induce the formation of unacceptable quantities of disulfonated and trisulfonated products. More preferably, the molar ratio of sulfonating agent to aromatic phosphine is greater than about 2/1. More preferably, the molar ratio of sulfonating agent to aromatic phosphine is less than about 5/1.

Usually, the aromatic phosphine is added as a solid or liquid melt to the sulfonating agent, preferably, oleum. Since the addition is exothermic, cooling should be provided to ensure that the reaction temperature does not exceed about 45° C. Cooling may be provided in the form of a cooling bath (e.g., ice or dry ice) or via contact of the reaction vessel with cooling coils filled with a refrigerant. Preferably, the temperature of the sulfonation is greater than about 20° C., more preferably, greater than about 30° C. Preferably, the temperature of the sulfonation is less than about 45° C., and more preferably, less than about 40° C. After the aromatic phosphine is added to the sulfonating agent, the synthesis mixture is heated to ensure complete reaction. The heating temperature is typically greater than about 50° C., preferably, greater than about 65° C., and more preferably, greater than about 75° C. The heating temperature is typically less than about 100° C., preferably, less than about 90° C., and more preferably, less than about 80° C. The heating time is generally greater than about 15 minutes, and preferably, greater than about 30 minutes. The heating time is generally less than about 10 hours, and preferably, less than about 7 hours. Depending upon the reaction conditions, the total reaction time may vary from a few minutes to several days, but more typically varies from about 4 hours to about 8 hours. The sulfonation is preferably conducted under an inert gaseous atmosphere substantially free of oxygen. Suitable inert gases include nitrogen, helium, neon, argon, xenon, krypton, carbon dioxide, carbon monoxide, hydrogen, or mixtures thereof, with nitrogen and the cheaper noble gases being preferred. The term "substantially free of oxygen" shall be taken to mean a concentration of oxygen no greater than about 0.1 volume percent, and preferably, no greater than about 0.01 volume percent. Avoidance of oxygen prevents or reduces oxidation of the aromatic phosphine to undesirable phosphine oxide.

After the sulfonation reaction is complete, the resulting synthesis mixture is treated to remove substantially all of the unconverted sulfonating agent. For the purposes of this invention, the phrase "substantially all of the unconverted sulfonating agent" shall mean typically greater than about 50, preferably, greater than about 70, more preferably, greater than about 80, even more preferably, greater than about 90, and most preferably, greater than about 98 weight percent of the unconverted sulfonating agent. Removal of the sulfonating agent is desirable, else sulfonation of the aromatic moieties may continue beyond the desired monosulfonated stage, thereby producing undesirable impurities. Moreover, since the subsequent partial neutralization step is exothermic, predilution, preferably with water, helps to dissipate the heat of neutralization. It is noted that the quench and removal step (process step (b)) need not be conducted as a separate step; but may, if desired, be carried out simultaneously with the partial neutralization step (c). If steps (b) and (c) are conducted simultaneously, then the neutralization step should employ a considerably dilute aqueous neutralizing agent both to quench the unconverted sulfonating agent and to dilute the neutralization solution for temperature control. Preferably, the treatment to quench and remove substantially all of the unconverted sulfonating agent is performed as a separate step prior to partial neutralization of the aromatic phosphine monosulfonate.

A preferred method of treatment at this stage involves quenching the synthesis mixture with water to convert substantially all of the unreacted oleum to aqueous sulfuric acid. The quantity of water used in the quench depends upon the initial amounts of aromatic phosphine and oleum present and the amount of oleum remaining unreacted. Moreover, the quantity of water is preferably sufficient to dissolve substantially all of the sodium sulfate that eventually forms in the first neutralization step to follow. The use of a large excess of water requires, however, concomitantly large equipment, thereby increasing the cost of the process. Accordingly, based on the amount of sodium sulfate expected to be produced, the skilled artisan can determine an appropriate quantity of water that balances the reaction requirements versus the size and cost of equipment. Since the addition of water to the product mixture is exothermic, the reaction mixture is cooled during the quench step with conventional cooling means as described hereinabove. Sufficient cooling is provided during the quench step to maintain a temperature greater than about 20° C., and preferably, greater than about 30° C. Typically, the temperature during the quench step is maintained less than about 45° C., and preferably, less than about 40° C. The quench step preferably employs degassed water and operates under an inert atmosphere, as described hereinbefore, so as to prevent oxidation of the phosphine. Up to this stage, the aromatic phosphine monosulfonate is present in an acid form wherein both the sulfonate group and at least one phosphorus atom are protonated.

In an important aspect of this invention, after or simultaneous with the quench step the product mixture is neutralized partially with an aqueous solution of a neutralizing agent (first neutralizing agent). The neutralization is intended to neutralize essentially completely the free sulfuric acid remaining in solution, while neutralizing only partially the acid groups on the aromatic phosphine monosulfonate. Unexpectedly, it has been discovered that the partial neutralization of the acid form of the aromatic phosphine monosulfonate produces a zwitterionic form of the aromatic phosphine monosulfonate, substantially all of which phase separates in substantially pure form from the aqueous product mixture. Advantageously, the phase separated zwitterionic compound takes the form of a solid or neat liquid layer separate from the liquid neutralization layer. The actual quantity of zwitterion that phase separates from solution depends upon the specific zwitterion concerned and its solubility limit in water. Accordingly, the phrase "substantially all of which aromatic phosphine monosulfonate zwitterion phase separates" shall be taken to mean that typically greater than about 70, preferably, greater than about 80, more preferably, greater than about 90, even more preferably, greater than about 95, and most preferably, greater than about 98 weight percent aromatic phosphine monosulfonate zwitterion formed phase separates from the neutralization solution.

More advantageously, the phase-separated zwitterion contains little if any quantities of undesirable disulfonated and trisulfonated aromatic phosphines; essentially no phosphine oxides and sulfites; and most importantly, little if any undesirable metal sulfate co-product. Most advantageously, the large quantity of metal sulfate produced on neutralization remains soluble in the aqueous liquid phase neutralization mixture. In contrast, the prior art describes complete neutralization of the acid form of the sulfonated product; and in so doing, all sulfonated organic phosphine products remain soluble in the aqueous neutralization mixture together with all forms of soluble impurities and by-products, including most prominently, the metal sulfate. Thus, by isolating the zwitterionic form of the aromatic phosphine monosulfonate, the process of this invention significantly simplifies work-up of the sulfonation product mixture and recovery of substantially pure aromatic phosphine monosulfonate product.

The zwitterionic form of the aromatic phosphine monosulfonate product may be represented, preferably, by formula (1) hereinabove. Note that the zwitterion, which is electronically neutral, contains two charged segments, specifically, a protonated, positively-charged, quadrivalent phosphorus atom and a deprotonated, negatively-charged sulfonate group. Analogous zwitterions can be drawn corresponding to the biphosphine and triphosphine formulas (4) and (5) hereinabove, wherein a sulfonate anion ($SO_3^-$) is substituted on an aryl group of $R^1$, and wherein any one of the phosphorus atoms is protonated, quadrivalent, and positively charged.

The partial neutralization is effected with an aqueous solution of a neutralizing agent, which comprises any base that produces the desired zwitterion product without precipitating unacceptable quantities of by-products and impurities. Preferably, the neutralizing agent (also referred to as the "first" neutralizing agent) is selected from the group consisting of Group 1 alkali metal hydroxides, Group 2 alkaline earth hydroxides, ammonia, ammonium hydroxide, ammonium carbonate, Group 1 alkali metal carbonates, water-soluble alkylamines, and mixtures thereof. The water-soluble alkylamines may include, for example, primary, secondary, and tertiary water-soluble alkyl amines, preferably, water-soluble $C_{1-8}$ alkyl amines, such as methylamine, ethylamine, propylamine, dimethylamine, and trimethylamine. Generally, it is advantageous to use a concentrated solution of base, because a substantial quantity of sulfuric acid remaining in the product mixture is required to be neutralized. Typically, the concentration of the neutralizing agent in aqueous solution is greater than about 2 N, and preferably, greater than about 4 N.-Typically, the concentration of the neutralizing agent in aqueous solution is less than about 10 N, and preferably, less than about 8 N. Generally, the neutralizing agent is added to the sulfonate product mixture slowly and with agitation, so that the temperature of the product mixture is maintained generally at a temperature greater than about 20° C., and preferably, greater than about 30° C. Typically, the temperature during neutralization is maintained at less than about 90° C., and preferably, less than about 80° C. Cooling or heating by conventional means may be employed to maintain the temperature in the desired range. Beneficially, the neutralization is conducted under an inert gaseous atmosphere; and the aqueous solution of neutralizing agent is degassed to remove oxygen. Suitable inert atmospheres, as mentioned hereinbefore, include nitrogen, helium, neon, argon, xenon, krypton, carbon dioxide, carbon monoxide, and hydrogen, with nitrogen and the cheaper noble gases being preferred. Exclusion of oxygen prevents oxidation of the phosphine to phosphine oxide.

Throughout the partial neutralization step, the pH of the product mixture is measured using a conventional pH-measuring means known to the skilled artisan. The partial neutralization step is complete when the pH of the product mixture reaches an equivalence point at which the aromatic phosphine monosulfonate in acid form has been converted essentially to its zwitterionic form. For determination of the pH endpoint of the neutralization, one skilled in the art is referred to principles of acid-base chemistry and titration graphs. For illustration, reference is made to FIG. 1, which comprises a graph of pH as a function of equivalents of base added to a product solution containing dicyclohexylphenylphosphine monosulfonate in acid form. As seen from FIG. 1, two endpoints are observed across the pH range from about 1 to about 11. The endpoints are observed at the two points of steepest positive slope of the curve. (FIG. 1, pH 3.8 and 8.5) Each equivalence point lies approximately mid-way on the steep slopes between the flatter bottom and top portions of the curve. Generally, the first endpoint occurs at a pH between about 2.0 and about 5.0 upon deprotonation of the sulfonate entity and formation of the zwitterion. In FIG. 1 related to the titration of dicyclohexylphenylphosphine monosulfonate, the first of these endpoints occurs at about pH 3.8. In practice, it is suitable to reach the first endpoint within plus or minus 1.0 pH unit (for example, 3.8±1.0 or all points in-between pH 2.8 and 4.8), and preferably, within plus or minus 0.5 pH unit (for example, 3.8±0.5 or all points in-between pH 3.3 and 4.3).

Generally, the second equivalence point occurs at a pH between about 6.0 and about 10.0 upon deprotonation of the phosphorous atom and formation of the aromatic phosphine monosulfonate salt, preferably, metal salt. In FIG. 1 related to the titration of dicyclohexylphenol-phosphine monosulfonate, the second of these endpoints occurs at about pH 8.5. In practice, it is suitable to reach the second endpoint within plus or minus 1.0 pH unit (for example, 8.5±1.0 or all points in-between pH 7.5 and 9.5), and preferably, plus or minus 0.5 pH unit (for example, 8.5±0.5 or all points in-between 8.0 and 9.0). These endpoint ranges may vary depending upon the specific aromatic phosphine monosulfonate involved. Accordingly, a pH titration curve should be predetermined for the selected aromatic phosphine monosulfonate in order to identify more precisely the desired equivalence point for obtention of the zwitterion.

As neutralization of the acid form of the aromatic phosphine monosulfonate proceeds, the zwitterionic form of the aromatic phosphine monosulfonate, which is insoluble in water, phase separates from the neutralization solution. If precipitated as a solid, the zwitterion may be recovered by any conventional means, such as filtration, centrifugation, ultra-centrifugation, or a combination thereof. If phase separated into a neat liquid phase, the zwitterion may be recovered by decantation from the liquid neutralization phase. The filtrate (or liquid neutralization phase) comprises a nearly saturated aqueous solution of metal sulfate, for example, sodium sulfate. Typically, the zwitterionic product may be washed one or more times with a solvent to remove residual sodium sulfate. Suitable solvents are those that are capable of dissolving metal sulfate without dissolving to an unacceptable extent the zwitterionic phosphine product. Non-limiting examples of suitable solvents include water and $C_{1-4}$ alcohols, such as methanol, preferably, water. The filtrate and washes are usually disposed as waste. Since the zwitterion is less prone to oxidation as compared with its solubilized acid counterpart, the filtration and washes can be conducted under air without the precautions heretofore employed to exclude oxygen.

The aromatic phosphine monosulfonate in zwitterionic form is typically obtained in a yield greater than about 60 weight percent, preferably, greater than about 70 weight percent, and more preferably, greater than about 80 weight percent, based on the weight of the reactant aromatic phosphine. The zwitterion and purity thereof can be evaluated by modern analytical techniques known to those of skill in the art, for example, by elemental analysis, $^1H$, $^{13}C$, and $^{31}P$ nuclear magnetic resonance (NMR), infrared, and ultraviolet spectroscopes. $^{31}P$ NMR is especially helpful in distinguishing a quadrivalent phosphorus atom in the zwitterion from a trivalent phosphorus in the reactant aromatic phosphine and a pentavalent phosphorus in the corresponding phosphine oxide. Absent from the zwitterion in unacceptable quantities are sodium sulfate, sodium sulfite, phosphine oxide, disulfonated and trisulfonated aromatic phosphines, and unconverted aromatic phosphine. Typically, the concentration of sodium sulfate is less than about 5 weight percent, preferably, less than about 1 weight percent. Typically, the concentration of sodium sulfite is less than about 1 weight percent, preferably, less than about 0.1 weight percent. Typically, the concentration of phosphine oxide is less than about 2 weight percent, preferably, less than about 1 weight percent. Typically, the combined concentration of di- and tri-sulfonated aromatic phosphines is less than about 1 weight percent, preferably, less than about 0.3 weight percent. Typically, the concentration of unconverted aromatic phosphine is less than about 4 weight percent, preferably, less than about 2 weight percent. Thus, in terms of purity, the isolated material comprises greater than about 87 weight percent aromatic phosphine monosulfonate in zwitterionic form, preferably, greater than about 95 percent by weight aromatic phosphine in zwitterionic form.

Optionally, the aromatic phosphine monosulfonate in zwitterionic form may be converted to an essentially pure aromatic phosphine monosulfonate in acid or salt form, as desired. In the salt, the phosphorus atom of the aromatic phosphine monosulfonate is trivalent and no longer protonated. In the acid form, a phosphorus atom is protonated and tetravalent. The sulfonate ion is either protonated (acid form), or associated with a cation, such as, a metal ion (typically monovalent, and preferably, a Group 1A metal ion), a quaternary ammonium ion ($NR^4_4{}^+$), or a quaternary phosphonium ion ($R^4_4P^+$) (intermolecular, not intramolecular), wherein as noted previously each $R^4$ may be the same or different and individually represents a substituted or unsubstituted monovalent hydrocarbyl radical having from 1 to about 20 carbon atoms. The acid form is obtained by combining the zwitterion with a polar liquid medium and back-titrating the zwitterion with acid. The salt is obtained by combining the zwitterion with a polar liquid medium and titrating the zwitterion with a base, such as, a Group 1 or 2 hydroxide or carbonate, or a quaternary ammonium hydroxide, or a quaternary phosphonium hydroxide. Preferably, the zwitterion is combined with a polar liquid medium to form a solution or slurry and then neutralized with a second neutralizing agent comprising a metal ion base, more preferably, a Group 1 or Group 2 hydroxide, most preferably, sodium or potassium hydroxide, to form the aromatic phosphine monosulfonate metal salt. The monosulfonated product in metal salt form is the catalytically active form when used as a ligand in hydroformylation processes.

The polar liquid medium may comprise any inorganic or organic compound that is liquid at a temperature between about 21° C. and about 100° C.; that is substantially non-reactive with the aromatic phosphine monosulfonate; and that has sufficient polarity to dissolve the aromatic phosphine monosulfonate salt. Preferably, the polar liquid medium does not dissolve residual metal sulfate to an unacceptable degree. Polar organic media that may be suitably employed include, for example, alcohols, preferably, $C_{1-4}$ alcohols, such as methanol, ethanol, propanol, and butanol; ketones, such as acetone; esters, such as methyl formate, methyl acetate, and ethyl acetate; nitriles, such as acetonitrile; and amides, such as dimethylformamide. Water is also an acceptable polar liquid medium. A preferred polar liquid medium comprises methanol or ethanol. The quantity of polar liquid medium used per gram of zwitterion typically ranges from about 5 g to about 100 g per g zwitterion. The zwitterion may be added to the polar liquid medium, or vice versa. Generally, the zwitterion is added to the polar liquid medium with stirring.

The second neutralizing agent may be identical to or different from the first neutralizing agent. Typically, the second neutralizing agent is provided in a neutralization solution of the same polar liquid medium used to contain or dissolve the zwitterion. Polar organic solvents, such as the aforementioned alcohols, ketones, esters, nitrites, and amides, are preferred. Typically, the concentration of second neutralizing agent in the neutralization solution is greater than about 0.1 N, and preferably, greater than about 0.5 N. Typically, the concentration of second neutralizing agent in the neutralization solution ranges from about 0.5 N to about 5 N. Generally, the second neutralizing agent is added slowly and with agitation to the polar liquid medium containing the zwitterion. The temperature during second neutralization is typically maintained at greater than about 20° C., preferably, greater than about 30° C. The temperature during second neutralization is typically maintained at less than about 45° C., preferably, less than about 40° C. The combination of the zwitterion with the polar liquid medium and subsequent neutralization are conducted under a blanket of inert gas; and the neutralizing agent is degassed for the purpose of reducing oxidation of the phosphine to phosphine oxide. Suitable inert gases have been described hereinbefore.

The second neutralization step is complete at a pH (equivalence point) or inflection point wherein the aromatic phosphine monosulfonate exists predominantly as a salt. In order to determine the pH of this equivalence point in aqueous solution, one skilled in the art is referred again to FIG. 1 plotting the pH of an aromatic phosphine monosulfonate as a function of equivalents of neutralizing agent added. The second endpoint, for deprotonation of the phosphorus atom, yields the salt of the aromatic phosphine monosulfonate. This second endpoint occurs at the point of greatest slope in a pH region roughly between about 6.0 and about 10.0, although such a range should not be limiting, inasmuch as the endpoint varies with the specific aromatic phosphine monosulfonated species. In a preferred embodiment, with reference to FIG. 1, the second neutralization endpoint is obtained at about pH 8.5±1.0 for the preferred dicyclohexylphenylphosphine monosulfonate sodium salt.

The skilled artisan will recognize that pH is not strictly defined for non-aqueous solutions. Consequently, if the second neutralization step is conducted in a polar organic solvent, such as the preferred methanol, or a mixture of organic solvent and water, then the endpoint of the neutralization, i.e., the "inflection point," is taken to be the second point of largest slope on a plot of any measure of hydrogen ion concentration versus equivalents of second neutralizing agent added. Since, generally, the actual hydrogen ion concentration correlates with readings on a conventional pH meter, a pH meter may be employed. Usually, the inflection point in polar organic solvent also falls in a pH range from about 6.0 to about 10.0. For purposes of calibrating the pH probe (electrode), a standard aqueous buffer solution of known pH can be prepared or obtained commercially. Reference is made to the following texts for pH ranges of standard aqueous buffer solutions: A. J. Gordon and R. A. Ford, *The Chemist's Companion: A Handbook of Practical Data, Techniques, and References*, Wiley-Interscience Publishers, John Wiley & Sons, 1972, pp. 71-74; and the *Handbook of Chemistry and Physics*, CRC Press, 1996, pp. 8-37 to 8-39. The art also describes standard buffer solutions for alcohol-aqueous mixtures. See, for example, T. Mussini, et al., "Criteria for Standardization of pH Measurements in Organic Solvents and Water," *Pure and Applied Chemistry*, 57 (1985), 865-876. The aforementioned references are incorporated herein by reference.

Thereafter, optionally, the liquid phase comprising the aromatic phosphine monosulfonate salt and polar liquid medium, can be extracted with any non-polar organic solvent capable of dissolving residual extraneous organic species, such as unconverted aromatic phosphine. Non-limiting examples of suitable non-polar solvents include aliphatic compounds, such as $C_{5-12}$ alkanes; and aromatic compounds, such as, toluene and xylene. The preferred solvent is a $C_{6-12}$ alkane, such as hexane, heptane, octane, nonane, decane, and the like; with hexane being more preferred. Typically, from about 0.1 to about 1.0 liter of non-polar solvent is employed per liter of solution containing the polar liquid medium and aromatic phosphine monosulfonate salt. Similar to other liquid phase process steps described hereinbefore, the extraction is also conducted under an inert gas atmosphere.

As a final and optional step, the aromatic phosphine monosulfonate salt, preferably, the metal salt, may be transferred from the polar liquid medium and dissolved in a second liquid medium, preferably, a solvent suitable for use in syntheses of transition metal-ligand complex catalysts. One means of effecting this liquid medium exchange comprises adding the desired solvent or second liquid medium to the polar liquid medium containing the aromatic phosphine monosulfonate salt and then removing the polar liquid medium. A preferred second liquid medium for the exchange is N-methyl-2-pyrrolidinone. The liquid medium exchange is blanketed under an inert gas so as to avoid oxidation of the phosphine to phosphine oxide. Suitable inert gases have been mentioned hereinbefore. After the second liquid medium is added, the first liquid medium can be removed by evaporation, distillation, decantation, extraction, or any other conventional separation means, resulting in a solution comprising the second liquid medium and aromatic phosphine monosulfonate salt.

In an alternative optional step, the aromatic phosphine monosulfonate salt may be recovered from the polar liquid medium by conventionally evaporating or distilling, preferably under reduced pressure, the polar liquid medium, preferably the polar organic solvent, more preferably, methanol. This optional procedure yields the aromatic phosphine monosulfonate salt as an essentially pure solid.

As a further option, the aromatic phosphine monosulfonate salt can be isolated from the polar liquid medium or the second liquid medium, as the case may be, by precipitation as a crystalline solid. Crystallization can be effected by conventional means, such as by cooling the liquid medium or partially evaporating the liquid medium.

The following example illustrates the invention, but should not be construed to limit the invention in any manner. One skilled in the art will recognize variations of the example that fall within the scope of the invention.

EXAMPLE

A synthesis was undertaken to prepare dicyclohexylphenylphosphine monosulfonate sodium salt (18 kg) as a 20 weight percent solution in N-methylpyrrolidinone (total solution—90 kg).

Figure 2:
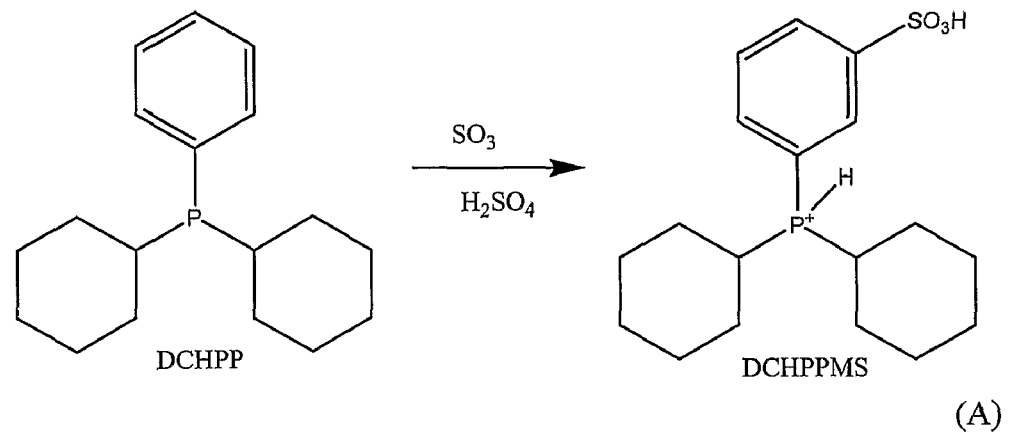
FIG. 2 illustrates a synthetic scheme according to the invention for preparing dicyclohexylphenylphosphine monosulfonate in zwitterionic form and as a sodium salt.
Figure 2:
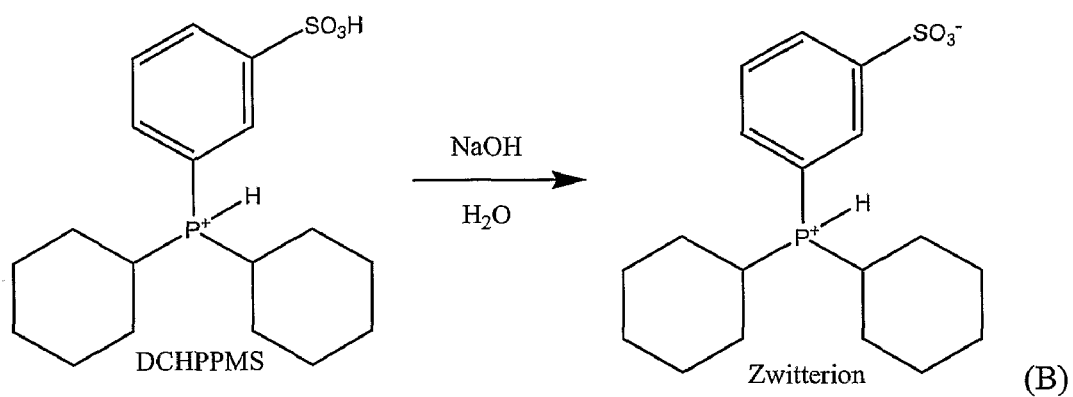
Figure 2:
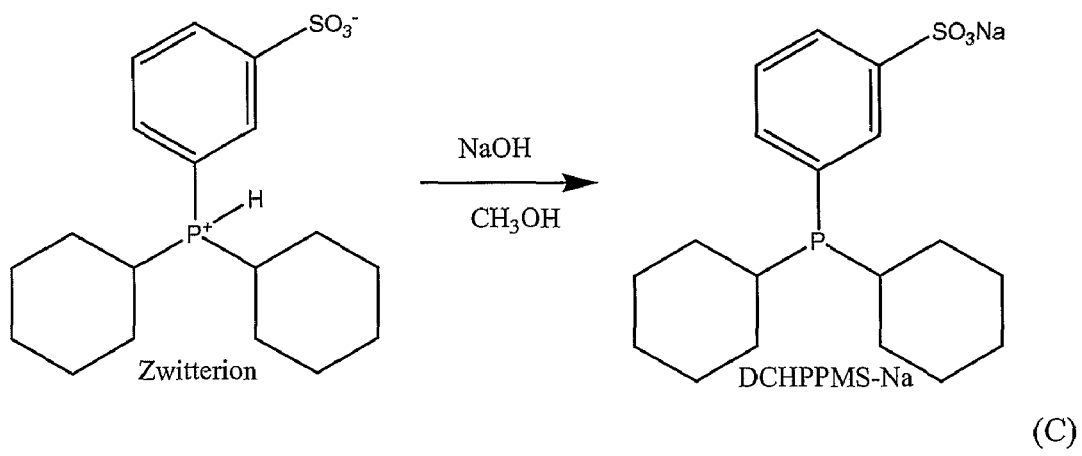

Reagents Used:
Dicyclohexylphenylphosphine (DCHPP)-16 kg (58.5 mol)
30% $SO_3$ oleum (fuming sulfuric acid) by weight—44 kg
Deionized water—250 kg
Aqueous sodium hydroxide (6.0 N NaOH/water)—110 L
Methanol—50 L
Methanolic sodium hydroxide (1.0 N NaOH/methanol)—50 L
Hexane—100 kg
N-Methyl-2-pyrrolidinone (NMP)—70 kg All solutions were handled under an inert atmosphere. Solids were exposed to air without deleterious effects. With reference to FIG. 2 (Reaction A), oleum (44 kg of 30 weight percent $SO_3$ fuming sulfuric acid) was added to a glass-lined reaction vessel under nitrogen. Solid dicyclohexylphenylphosphine (DCHPP) (16 kg, 58.5 mol) was added to the reaction vessel in 4 kg aliquots. The addition was exothermic. The reaction vessel was cooled during the solids addition, and the DCHPP was added sufficiently slowly to keep the reaction temperature between 30° C. and 40° C. After the solids were added, the reaction vessel was heated to 80° C. for 6 hours. The reaction generated dicyclohexylphenyl phosphine monosulfonate (DCHPPMS) as a sulfuric acid solution, thus fully protonated in acid form.

The DCHPPMS/sulfuric acid reaction mixture was quenched to removed unconverted oleum by adding the reaction mixture to degassed, deionized water (250 L). This addition was exothermic; therefore, heat was removed by cooling the solution while adding the reaction mixture to the water at a sufficiently slow rate to keep the temperature between 30° C. and 40° C.

With reference to FIG. 2 (Reaction B), after quenching the unreacted oleum, the DCHPPMS reaction mixture was partially neutralized to a pH of 3.8±0.5 by adding aqueous sodium hydroxide (6N) in degassed water essentially free of oxygen. Sufficient base was added to neutralize all of the sulfuric acid and unreacted $SO_3$ as well as partially the DCHPPMS. The neutralization required 660 moles of sodium hydroxide or about 110 L of sodium hydroxide (6N) solution. Throughout the neutralization, an exotherm was controlled by adding the sodium hydroxide solution at a sufficiently slow rate to keep the temperature between 30° C. and 40° C. The partial neutralization generated the DCHPPMS zwitterion as a filterable solid that precipitated from the solution. The end of the addition was determined by monitoring pH, by means of a conventional pH meter, to an endpoint of pH 3.8±0.5.

The zwitterionic precipitate was collected by filtration and washed with water. The filtrate, about 400 L of nearly saturated sodium sulfate solution, and the water washes were discarded as waste. A theoretical yield of DCHPPMS zwitterion was calculated to be 20.7 kg (100 percent). The experiment generated 16.6 kg product (80 percent yield). $^{31}$P NMR showed that greater than 99 weight percent of the phosphorus was present as the zwitterion with phosphine oxide at less than 1.0 weight percent and unconverted aromatic phosphine at less than 0.1 weight percent. $^{31}$P NMR spectrum: 16.9 ppm, singlet, integral 189, assigned to phosphonium salt P atom; 46.4 ppm, singlet, integral 1.00, assigned to phosphine oxide P atom. $^1$H NMR: 7.94 ppm, doublet, integral 1.0; 7.83 ppm, doublet, integral 1.0; 7.69 ppm, triplet, integral 1.0; 7.54 ppm, triplet, integral 1.0; 2.46 ppm, singlet, integral 1.0; 1.89 ppm, multiplet, integral 2.0; 1.8-0.8 ppm, multiplet, integral 20.

With reference to FIG. 2 (Reaction C), the DCHPPMS zwitterion was suspended in methanol for neutralization to dicyclohexylphenylphosphine monosulfonate sodium salt. Methanol (50 L air-free) was added to a reaction vessel under nitrogen. The DCHPPMS zwitterion was added to the vessel to form a slurry. After the solid was added, a methanolic solution of sodium hydroxide (1.0 N) was added to the slurry to neutralize the zwitterion at a rate sufficient to keep the temperature of the mixture between 30° C. and 40° C. For a zwitterion charge of 16.6 kg, then 50 L of sodium hydroxide solution were required. The solid zwitterion dissolved as it was neutralized. The end of the addition was determined by monitoring pH, using a conventional pH meter, to an end point of pH 8.5±0.5. The neutralized solution was filtered to remove any residual solid sodium sulfate or other solids that might have been present, yielding a methanolic solution of dicyclohexylphenylphosphine monosulfonate sodium salt (DCHPPMS—Na).

Figure 3:
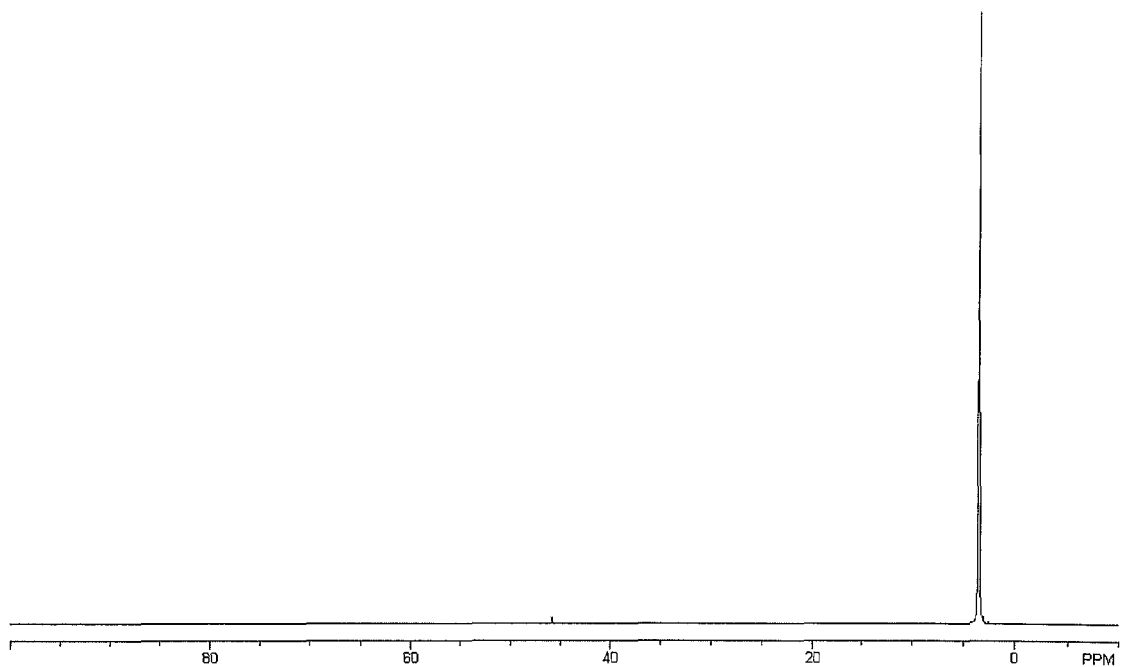
FIG. 3 illustrates a $^{31}P$ nuclear magnetic resonance spectrum of dicyclohexylphenylphosphine monosulfonate sodium salt.

Hexane (50 L) was added to the DCHPPMS—Na/methanol solution and the resulting two-phase mixture was agitated to wash out hexane-soluble species. Then, the hexane layer was decanted from the methanol layer. The hexane wash and decant were repeated a second time. Then, N-methyl-2-pyrrolidinone (NMP) (70 kg) was added to the methanol solution. The methanol was removed from the solution by distillation keeping the kettle temperature below 110° C. Methanol was condensed in the overhead at 10° C. when the distillation was conducted at 60 mm Hg absolute pressure. A yield of dicyclohexylphenyl-phosphine monosulfonate sodium salt (85-90 kg) was obtained as a 20 weight percent solution in NMP. The purity of the salt was such that greater than 99 weight percent of the phosphorous was present as DCH-PPMS—Na, as determined by $^{31}$P-NMR. (FIG. 3)

$^{31}$P NMR spectrum (refer to FIG. 3): 3.4 ppm, singlet, integral 212, assigned to product phosphine P atom; 46.3 ppm, singlet, integral 1.00, assigned to phosphine oxide P atom; 2.3 ppm, singlet, integral 0.8, assigned to unreacted starting phosphine P atom. $^1$H NMR: 7.69 ppm, doublet, integral 1.0; 7.60 ppm, doublet, integral 1.0; 7.42-7.30 ppm, multiplet, integral 2.0; 1.88 ppm, multiplet, integral 2.0; 1.8-0.8 ppm, multiplet, integral 20. $^{13}$C NMR: 147.2, 134.5, 134.0, 131.5, 127.5, 126.2, 31.9, 29.7, 28.6, 26.7, 26.4, 26.2. inductively coupled plasma atomic adsorption spectroscopy (ICP) analysis indicated that the DCHPPMS—Na contained less than 50 ppm by weight magnesium, calcium, and chloride. Ion chromatography showed that the DCHPPMS—Na contained less than 500 ppm by weight sodium sulfate and less that 100 ppm by weight sodium sulfite.

What is claimed is:

1. A process of preparing an aromatic phosphine monosulfonate in zwitterionic form, the process comprising:
   (a) contacting an aromatic phosphine with a sulfonating agent under reaction conditions sufficient to obtain a product mixture comprising an acid form of an aromatic phosphine monosulfonate, in which the sulfonate group and phosphorus atom are both protonated, and unconverted sulfonating agent;
   (b) quenching or removing substantially all of the unconverted sulfonating agent;
   (c) partially neutralizing the acid form of the aromatic phosphine monsulfonate with an aqueous solution of a neutralizing agent (first neutralizing agent) to an endpoint at a pH between 2.0 and 5.0 under conditions sufficient to phase separate substantially all of the aromatic phosphine monosulfonate in zwitterionic form, namely the aromatic phosphine monosulfonate in which the sulfonate group is deprotonated and the phosphorus atom is protonated; and
   (d) collecting the zwitterionic form of the aromatic phosphine monosulfonate as a solid or neat liquid.

2. The process of claim 1 wherein after step (d), the following step is conducted: (e) adding the zwitterionic form of the aromatic phosphine monosulfonate to a liquid medium to form a solution or slurry, and neutralizing the zwitterion with a second neutralizing agent under conditions sufficient to yield an aromatic phosphine monosulfonate salt.

3. The process of claim 1 wherein the aromatic phosphine comprises at least one aryl group and one trivalent phosphorus and is represented by the following formula:

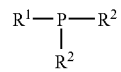

wherein $R^1$ represents a monovalent hydrocarbyl radical containing from 1 to 30 carbon atoms selected from aryl, alkaryl, and aralkyl monovalent radicals; and each $R^2$ individually represents a monovalent hydrocarbyl radical containing from 1 to 30 carbon atoms.

4. The process of claim 3 wherein the aromatic phosphine is a dicycloalkylarylphosphine.

5. The process of claim 4 wherein the aromatic phosphine is dicyclohexylphenylphosphine.

6. The process of claim 1 wherein the sulfonating agent is oleum (fuming sulfuric acid), optionally, having a sulfur trioxide concentration from 20 to 30 weight percent.

7. The process of claim 1 wherein in step (a) the aromatic phosphine is added under an inert gas atmosphere to the sulfonating agent at a temperature greater than 20° C. and less than 45° C., and thereafter the resulting synthesis mixture is heated under an inert gas atmosphere at a temperature greater than 50° C. and less than 100° C.

8. The process of claim 1 wherein the quenching step (b) is conducted with water at a temperature greater than 20° C. and less than 45° C., optionally, under an inert gas atmosphere.

9. The process of claim 1 wherein the partial neutralization step (c) is conducted at a temperature greater than 20° C. and less than 90° C. under an inert gas atmosphere; and the neutralizing agent is selected from the group consisting of Group 1 alkali hydroxides, Group 2 alkaline earth hydroxides, ammonia, ammonium hydroxide, Group 1 alkali carbonates, water-soluble alkylamines, and mixtures thereof.

10. The process of claim 1 wherein the zwitterion is represented by the following formula:

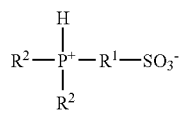

wherein $R^1$ represents a sulfonated monovalent hydrocarbyl radical containing from 1 to 30 carbon atoms selected from aryl, alkaryl, and aralkyl monovalent radicals, such that the aryl group is sulfonated as shown; and each $R^2$ individually represents a monovalent hydrocarbyl radical containing from 1 to 30 carbon atoms.

11. The process of claim 1 wherein after the zwitterion is recovered in step (d) as a solid or neat liquid, the zwitterion is washed with water.

12. (previously presented The process of claim 2 wherein the zwitterion recovered as a solid or neat liquid is suspended or dissolved in a polar organic liquid medium selected from the group consisting of water, alcohols, ketones, esters, nitriles, amides, and mixtures thereof.

13. The process of claim 12 wherein the zwitterion suspended or dissolved in the polar organic liquid medium is neutralized with a neutralizing agent (second neutralizing agent) selected from the group consisting of Group 1 alkali hydroxides, Group 2 alkaline earth hydroxides, ammonia, ammonium hydroxide, Group 1 alkali carbonates, water-soluble amines, and mixtures thereof to form the corresponding aromatic phosphine monosulfonate salt.

14. The process of claim 13 wherein the neutralization step is conducted at a temperature greater than 20° C. and less than 45° C. under an inert gas atmosphere.

15. The process of claim 13 wherein the neutralization step is conducted to an equivalence or inflection point at a pH between 6.0 and 10.0.

16. The process of claim 13 wherein after the second neutralization step, the polar organic liquid medium containing the aromatic phosphine monosulfonate salt is subjected to solvent exchange with a second liquid medium; and optionally, prior to the solvent exchange the polar organic liquid medium containing the aromatic phosphine monosulfonate salt is extracted with a non-polar liquid hydrocarbon.

17. The process of claim 16 wherein the second liquid medium comprises N-methyl-2-pyrrolidinone.

18. The process of claim 13 wherein after the second neutralization step, the polar organic liquid medium is removed by extraction, distillation, or evaporation to yield the aromatic phosphine monosulfonate salt as a solid; or alternatively, wherein after second neutralization, the aromatic phosphine monosulfonate salt is crystallized out of the polar organic liquid medium.

19. The process of claim 1, steps (a) through (c) being conducted in an inert gas atmosphere selected from the group consisting of nitrogen, helium, neon, argon, xenon, krypton, carbon dioxide, carbon monoxide, hydrogen, and mixtures thereof.

20. The process of claim 1 wherein the aromatic phosphine is a dialkylphenylphosphine; wherein the sulfonating agent is oleum; and wherein the neutralizing agent is an Group 1 alkali hydroxide.

21. The process of claim 1 wherein process step (c) is conducted after process step (b).

22. The process of claim 1 wherein process steps (b) and (c) are conducted simultaneously.

23. A process of preparing dicyclohexylphenylphosphine monosulfonate alkali metal salt comprising:
   (a) contacting dicyclohexylphenylphosphine with oleum under reaction conditions sufficient to obtain a product mixture comprising an acid form of dicyclohexylphenylphosphine monosulfonate and unreacted oleum;
   (b) quenching or removing substantially all of the unconverted oleum with water;
   (c) partially neutralizing the acid form of the dicyclohexylphenylphosphine monosulfonate to a pH of 3.8±1.0 with an aqueous solution of an alkali metal hydroxide so as to precipitate substantially all of the dicyclohexylphenylphosphine monosulfonate in zwitterionic form;
   (d) collecting a solid precipitate comprising the zwitterionic form of the dicyclohexylphenylphosphine monosulfonate;
   (e) combining the solid zwitterionic form of the dicyclohexylphenylphosphine monosulfonate with methanol to form a solution or slurry;
   (f) neutralizing the zwitterion in the methanolic solution or slurry with an alkali metal hydroxide to a pH of 8.5+1.0 to yield dicyclohexylphenylphosphine monosulfonate alkali metal salt in methanol solution; then optionally, extracting the methanolic solution or slurry with a non-polar hydrocarbon; and
   (g) optionally, exchanging the methanol for N-methyl-2-pyrrolidinone so as to obtain a solution of dicyclohexylphenylphosphine monosulfonate alkali metal salt in N-methyl-2-pyrrolidinone.

24. The process of claim 23 wherein the dicyclohexylphenyl-phosphine monosulfonate alkali metal salt is dicyclohexylphenylphosphine monosulfonate sodium salt.

* * * * *